(12) United States Patent
Faict et al.

(10) Patent No.: US 7,445,801 B2
(45) Date of Patent: Nov. 4, 2008

(54) STABLE BICARBONATE-BASED SOLUTION IN A SINGLE CONTAINER

(75) Inventors: Dirk Faict, Assenede (BE); Annick Duponchelle, Brussels (BE); Michel Taminne, Brussels (BE); Patrick Balteau, Bothey (BE); Francesco Peluso, Heverlee (BE)

(73) Assignees: Baxter International Inc., Deerfield, IL (US); Baxter Healthcare S.A, Zurich (CH)

( * ) Notice: Subject to any disclaimer, the term of this patent is extended or adjusted under 35 U.S.C. 154(b) by 0 days.

(21) Appl. No.: 10/165,482

(22) Filed: Jun. 7, 2002

(65) Prior Publication Data

US 2003/0232093 A1 Dec. 18, 2003

(51) Int. Cl.
  *A61K 33/00* (2006.01)
  *A61K 31/047* (2006.01)
  *A61K 31/195* (2006.01)
  *A61K 31/7004* (2006.01)
  *A61P 7/08* (2006.01)
  *B01D 61/24* (2006.01)

(52) U.S. Cl. .................. 424/717; 210/645; 210/646; 424/677; 424/682; 424/722; 514/23; 514/561; 514/738; 604/403; 604/408

(58) Field of Classification Search ............. 424/717
See application file for complete search history.

(56) References Cited

U.S. PATENT DOCUMENTS

| | | | |
|---|---|---|---|
| 3,878,664 A | 4/1975 | Zinke | |
| 4,372,100 A | 2/1983 | Miller et al. | |
| 4,396,383 A | 8/1983 | Hart | |
| 4,397,392 A | 8/1983 | Runck et al. | |
| 4,465,488 A | 8/1984 | Richmond et al. | |
| 4,489,535 A | 12/1984 | Veltman | |
| 4,584,176 A | 4/1986 | Oliver et al. | |
| 4,630,727 A | 12/1986 | Feriani et al. | |
| 4,663,166 A | 5/1987 | Veech | |
| 4,756,838 A | 7/1988 | Veltman | |
| 4,761,237 A | 8/1988 | Alexander et al. | |
| 4,863,714 A | 9/1989 | Sovak et al. | |
| 4,879,280 A | 11/1989 | Seyffart et al. | |
| 4,959,175 A | 9/1990 | Yatzidis | |
| 5,011,826 A | 4/1991 | Steudle et al. | |
| 5,039,609 A | 8/1991 | Klein | |
| 5,092,838 A | 3/1992 | Faict et al. | |
| 5,098,202 A | 3/1992 | Rosenbaum | 383/67 |
| 5,100,677 A | 3/1992 | Veech | |
| 5,141,492 A | 8/1992 | Dadson et al. | |
| 5,211,643 A | 5/1993 | Reinhardt et al. | |
| 5,296,242 A | 3/1994 | Zander | |
| 5,383,324 A | 1/1995 | Segers et al. | |
| 5,423,421 A | 6/1995 | Inoue et al. | |
| 5,431,496 A | 7/1995 | Balteau et al. | |
| 5,462,526 A | 10/1995 | Barney et al. | |
| 5,509,898 A | 4/1996 | Isono et al. | |
| 5,536,469 A | 7/1996 | Jonsson et al. | |
| 5,560,403 A | 10/1996 | Balteau et al. | |
| 5,601,730 A | 2/1997 | Page et al. | |
| 5,610,170 A | 3/1997 | Inoue et al. | |
| 5,706,937 A | 1/1998 | Futagawa et al. | |
| 5,780,438 A | 7/1998 | Gilchrist et al. | 514/21 |
| 5,827,820 A | 10/1998 | duMoulin et al. | |
| 5,853,388 A | 12/1998 | Semel | |
| 5,871,477 A | 2/1999 | Isono et al. | |
| 5,945,129 A | 8/1999 | Knerr et al. | |
| 6,013,294 A | 1/2000 | Bunke et al. | |
| 6,020,007 A | 2/2000 | Veech | |
| 6,232,128 B1 | 5/2001 | Iguchi et al. | |
| 6,323,182 B1 | 11/2001 | Linden et al. | |
| 2003/0013765 A1 | 1/2003 | Veech | |

FOREIGN PATENT DOCUMENTS

| | | |
|---|---|---|
| DE | 19748290 A1 | 5/1999 |
| EP | 0 083 360 B1 | 7/1983 |
| EP | 0 165 933 B1 | 1/1986 |
| EP | 0 209 607 B1 | 1/1987 |
| EP | 0086553 | 4/1987 |
| EP | 0086553 B1 | 4/1987 |
| EP | 0 249 667 B1 | 12/1987 |
| EP | 0 277 868 A2 | 8/1988 |

(Continued)

OTHER PUBLICATIONS

West online, file Derwent, Acc. No. 1996-349174, JP 08164199 (1996), Abstract.*

(Continued)

*Primary Examiner*—Johann Richter
*Assistant Examiner*—Frank I Choi
(74) *Attorney, Agent, or Firm*—Paula J. Kelly; Bell, Boyd & Lloyd LLP

(57) ABSTRACT

Stable single bicarbonate-based solutions are provided. The bicarbonate-based single solution of the present invention includes at least calcium and bicarbonate and is stored or packaged in a sterile manner within a container with a gas barrier. The single solutions of the present invention can remain stable for three months or more. In this regard, the stable and single bicarbonate-based solutions of the present invention can be readily and effectively used during medical therapy, such as dialysis therapy.

18 Claims, 1 Drawing Sheet

FOREIGN PATENT DOCUMENTS

| | | |
|---|---|---|
| EP | 0 278 100 A2 | 8/1988 |
| EP | 0 399 549 A1 | 11/1990 |
| EP | 0 399 918 A2 | 11/1990 |
| EP | 0 417 478 A1 | 3/1991 |
| EP | 0 437 274 A1 | 7/1991 |
| EP | 0 439 061 B1 | 7/1991 |
| EP | 0 457 960 A2 | 11/1991 |
| EP | 0 481 257 A1 | 4/1992 |
| EP | 0 613 688 A1 | 9/1994 |
| EP | 0 647 145 B1 | 4/1995 |
| EP | 0 776 649 A2 | 6/1997 |
| EP | 0 935 967 A2 | 8/1999 |
| EP | 1166787 A2 | 1/2002 |
| FR | 2 753 099 A1 | 3/1998 |
| JP | 56164113 A2 | 12/1981 |
| JP | 57-056422 | 4/1982 |
| JP | 2304026 | 12/1990 |
| JP | EP0437274 | 1/1991 |
| JP | 3195561 A2 | 8/1991 |
| JP | 5105633 A2 | 4/1993 |
| JP | 6105905 A2 | 4/1994 |
| JP | 7252137 A2 | 10/1995 |
| JP | 8131542 A2 | 5/1996 |
| JP | 08-164199 | 6/1996 |
| JP | 08164199 | 6/1996 |
| JP | 8164199 A1 | 6/1996 |
| JP | 9087182 A2 | 3/1997 |
| JP | 9110703 A2 | 4/1997 |
| JP | 09-301860 | 11/1997 |
| JP | 9301875 A2 | 11/1997 |
| JP | 10201821 A2 | 8/1998 |
| JP | 11-9659 | 1/1999 |
| JP | 11-019178 A2 | 1/1999 |
| JP | 11004872 A2 | 1/1999 |
| JP | 2000-51348 | 2/2000 |
| JP | 2000-80033 | 3/2000 |
| JP | 3271650 B2 | 1/2002 |
| WO | WO 86/00239 | 1/1986 |
| WO | WO 86/03407 A1 | 6/1986 |
| WO | WO 87/03808 | 7/1987 |
| WO | WO 87/03809 A1 | 7/1987 |
| WO | WO 91/18610 A1 | 12/1991 |
| WO | WO 93/24108 | 12/1993 |
| WO | WO 95/19778 A1 | 7/1995 |
| WO | WO 96/01118 A1 | 1/1996 |
| WO | WO 97/05851 A1 | 2/1997 |
| WO | WO 98/10733 A1 | 3/1998 |
| WO | WO 98/33535 | 8/1998 |
| WO | WO 99/01144 A1 | 1/1999 |
| WO | WO 99/09953 A1 | 3/1999 |
| WO | WO 01/21233 A1 | 3/2001 |

OTHER PUBLICATIONS

Mehta et al., *Regional citrate anticoagulation for continuous arteriovenous hemodialysis in critically ill patients*, Kidney International, vol. 38 (1990), pp. 976-981.

van Bommel et al., *Continuous Renal Replacement Therapy for Critically Ill Patients: An Update*, Journal of Intensive Care Medicine, vol. 9, No. 6, Nov.-Dec. 1994, pp. 265-280.

Uthoff et al., *Improved Correction of Acidosis in Acute Renal Failure Using a Bicarbonate Buffered Substitution Solution*, Nephrology (1997), Suppl. 1, P1598.

Thomas et al, *Comparison of lactate and bicarbonate buffered haemofiltration fluids: use in critically ill patients*, Nephrology Dialysis Transplantation, (1997), vol. 12, pp. 1212-1217.

Manns et al., *Continuous Renal Replacement Therapies: An Update*, American Journal of Kidney Diseases, vol. 32, No. 2 Aug. 1998; pp. 185-207.

Feriani et al., *Acid-base balance and replacement solutions in continuous renal replacement therapies*, Kidney International, vol. 53, Suppl. 66 (1998), pp. S-156-S-159.

Heering et al., *The use of different buffers during continuous hemofiltration in critically ill patients with acute renal failure*, Intensive Care Medical (1999) vol. 25, pp. 1244-1251.

Zimmerman et al., *Continuous veno-venous haemodialysis with a novel bicarbonate dialysis solution: prospective cross-over comparison with a lactate buffered solution*, Nephrology Dialysis Transplantation, (1999) vol. 14, pp. 2387-2391.

Heering et al., *Acid-base balance and substitution fluid during continuous hemofiltration*, Kidney International, vol. 56, Suppl. 72 (1999) pp. S-37-S-40.

Lutkes et al., *Continuous venovenous hemodialysis treatment in critically ill patients after liver transplantation*, Kidney International, vol. 56 Suppl. 72 (1999) pp. S-71-S-74.

Kierdorf et al., *Lactate- or bicarbonate-buffered solutions in continuous extracorporeal renal replacement therapies*, Kidney International, vol. 56, Suppl. 72 (1999) pp. S-32-S-36.

Barenbrock et al., *Effects of bicarbonate- and lactate-buffered replacement fluids on cardiovascular outcome in CVVH patients*, Kidney International, vol. 58 (2000) pp. 1751-1757.

Manahan et al., *Peritoneal Dialysis using bicarbonate-containing solution sterilized by ultrafiltration*, The International Journal of Artificial Organs, vol. 14 No. 8, 1999, pp. 463-465.

Murphy et al., *Use of an Artificial Kidney*, vol. 40, 1952, pp. 436-444.

Tjiang, Boen San, *A Clinical Study of Factors Governing its Effectiveness*, Peritoneal Dialysis, p. 76, Van Gorcum & Co., Assen, The Netherlands (1959).

Feriani et al., *Short-Term Clinical Study with Bicarbonate-Containing Peritoneal Dialysis Solution*, Peritoneal Dialysis International, vol. 13, pp. 296-301 (1993).

*The Merck Index*, 12th Ed., Merck Research Laboratories, Whitehouse Station, NJ, 9 1472 (1996).

Odel et al., *Peritoneal Lavage as an Effective Means of Extraenal Excretion. A Clinical Appraisal*, American Journal of Medicine, vol. 9, 63-88 (1950).

Schambye et al., *The Cytotoxicity of Continuous Ambulatory Peritoneal Dialysis Solutions with Different Bicarbonate/Lactate Ratios*, Peritoneal Dialysis International vol. 13, Suppl. 2, Oct. 1-4, pp. S116-S118 (1994).

Schambye et al., *Bicarbonate-versus Lactate-Based CAPD fluids: A Biocompatibility Study in Rabbits*, Peritoneal Dialysis International, vol. 12, pp. 281-286 (1992).

Simonsen et al., *Less Infusion Pain and Elevated Level of Cancer Antigen 125 by the Use of a New and More Biocompatible PD Fluid*, Advances in Peritoneal Dialysis, vol. 12, pp. 156-160 (1996).

Ing., et al., *Bicarbonate-Buffered Peritoneal Dialysis*, The International Journal of Artificial Organ, vol. 8, No. 3, p. 121-124 (1985).

Zhou et al., *Effects of an Acidic, Lactate-Based Peritoneal Dialysis Solution and its Euhydric, Bicarbonate-Based Counterpart on Neutrophilic Interacellular pH*, Int. J. Artif. Organs, vol. 16, No. 12, pp. 816-819 (1993).

American Society for Artificial Internal Organs, 1994 Abstracts, pp. 110.

Faller et al., *Loss of Ultrafiltration in Continuous Ambulatory Peritoneal Dialysis: A Role for Acetate*, Peritoneal Dialysis Bulletin, Jan.-Mar. 1984, pp. 10-13.

Ing et al., *Lactate-Containing Peritoneal Dialysis Solutions*, International J. of Artificial Organs, vol. 16, No. 10, 1993, pp. 688-693.

Ing et al., *Lactate-Containing Versus Bicarbonate-Containing Peritoneal Dialysis Solutions*, Peritoneal Dialysis International, vol. 12, pp. 276-277.

Ing et al., *Preparation of Bicarbonate-Containing Dialysate for Peritoneal Dialysis*, International J. of Artificial Organs, vol. 6, No. 4, 1983, pp. 217-218.

Manahan et al., *Effects of Bicarbonate-Containing Versus Lactate-Containing Peritoneal Dialysis Solutions on Superoxide Production by Human Neutrophils*, Artificial Organs, vol. 13, No. 6, 1989, pp. 495-497.

Richardson et al., *Bicarbonate, L-Lactate, and D-Lactate Balance in Intermittent Peritoneal Dialysis*, Peritoneal Dialysis Bulletin, vol. 6, No. 4, 1986, pp. 178-185.

Yatzidis, Hippocrates, *A New Stable Bicarbonate Dialysis Solution for Peritoneal Dialysis: Preliminary Report*, Peritoneal Dialysis International, vol. 11, pp. 224-227.

European communication dated Apr. 25, 2008 (4 pgs.).

\* cited by examiner

STABLE BICARBONATE-BASED SOLUTION IN A SINGLE CONTAINER

BACKGROUND OF THE INVENTION

The present invention relates generally to medical treatments. More specifically, the present invention relates to solutions used for medical therapy including dialysis therapy, infusion therapy or the like.

Due to disease, insult or other causes, the renal system can fail. In renal failure of any cause, there are several physiological derangements. The balance of water, minerals (e.g., Na, K, Cl, Ca, P, Mg, $SO_4$) and the excretion of a daily metabolic load of fixed ions is no longer possible in renal failure. During renal failure, toxic end products of nitrogen metabolism (e.g., urea, creatinine, uric acid, and the like) can accumulate in blood and tissues.

Dialysis processes have been devised for the separation of elements in a solution by diffusion across a semi-permeable membrane (diffusive solute transport) across a concentration gradient. Examples of dialysis processes include hemodialysis, peritoneal dialysis, hemofiltration and hemodiafiltration.

Hemodialysis treatment utilizes the patient's blood to remove waste, toxins, and excess water from the patient. The patient is connected to a hemodialysis machine and the patient's blood is pumped through the machine. Needles or catheters are inserted into the patient's veins and arteries to connect the blood flow to and from the hemodialysis machine. Waste, toxins, and excess water are removed from the patient's blood and the blood is infused back into the patient. Hemodialysis treatments can last several hours and are generally performed in a treatment center about three or four times per week.

To overcome the disadvantages often associated with classical hemodialysis, other techniques were developed, such as peritoneal dialysis, hemofiltration and hemodiafiltration. Peritoneal dialysis utilizes the patient's own peritoneum as a semipermeable membrane. The peritoneum is the membranous lining of the body cavity that, due to the large number of blood vessels and capillaries, is capable of acting as a natural semipermeable membrane.

In peritoneal dialysis, a sterile dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base, electrolyte and fluid balance to be returned to the blood. The dialysis solution is simply drained from the body cavity through the catheter. Examples of different types of peritoneal dialysis include continuous ambulatory peritoneal dialysis, automated peritoneal dialysis and continuous flow peritoneal dialysis.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter (post dilution).

In addition to the removal of metabolic products, one of the most important problems of every kidney replacement therapy, such as hemodialysis, hemofiltration and peritoneal dialysis, lies in the correction of metabolic acidosis. For this reason, the dialysis solutions used in each of these processes contain a buffer.

Three common buffers often used in dialysis solutions are bicarbonate, lactate and acetate. While initially bicarbonate was the primary buffer used in dialysis solutions, over time lactate and acetate were used as substitutes for bicarbonate. This was due to the difficulty in preparation and storage of bicarbonate-buffered dialysis solutions. Lactate and acetate buffers are known to provide greater stability in use over the previous bicarbonate-buffered solutions.

However, since bicarbonate ions provide advantages over acetate or lactate ions, bicarbonate is again surfacing as the primary buffer used in dialysis solutions. Tests have been conducted that indicate patients exhibit a better tolerance for bicarbonate dialysis solutions. In patients with a multiple organ failure, bicarbonate-buffered solutions are preferred because of the lack of metabolic interference. Further, certain treatments require sterile dialysis solutions containing bicarbonate, calcium and magnesium.

But, in the presence of bicarbonate, these ions can form calcium carbonate and magnesium carbonate, respectively, which at increased pHs typically precipitate from the solution. To initially remedy this problem, bicarbonate solutions are often made from concentrates, ranging from slightly concentrated, two-fold or less, to much more concentrated solutions. Further, the bicarbonate on the one hand and calcium and/or magnesium on the other hand are included in separate concentrates and stored separately prior to use. For example, the concentrates can be stored in separate containers or separate chambers of a multi-chamber container. The bicarbonate concentrate and the concentrate of electrolytes that can include calcium, magnesium and the like are then mixed just prior to use to prevent the precipitation of carbonates.

However, the use of a multi-chamber container or individual containers to separately store the bicarbonate concentrate and the electrolyte concentrate prior to use can increase the amount of time and effort that is needed to perform dialysis therapy. With the use of a bicarbonate-based solution in a multi-chamber container, the patient is typically required to break a frangible to allow the concentrates to mix prior to use. Further, if a gas barrier overpouch is used with the multi-chamber container, the overpouch is typically removed prior to mixing. If the gas barrier overpouch is not removed, the breaking of the frangible can damage the gas barrier, thus causing a loss of long term solution stability.

Further, the use of a multiple number of individual containers to separately store the concentrates prior to mixing can require additional handling and storage capacity. U.S. Pat. No. 5,296,242 ("Zander") describes the use of a stable aqueous solution in the form of two separately stored single solutions, one containing a metabolizable organic acid, and the other alkali bicarbonate and alkali carbonate. The Zander patent relates to adjusting the pH of the dextrose compartment with an organic acid; the dextrose compartment is adjusted to a pH range of 4.0 to 6.0. Not only do the inventors believe a physiological solution will not be achieved with such a high pH for the dextrose component, problems arise from the use of organic acids. For example, in patients with liver failure the body has difficulty in metabolizing organic acids, and it is therefore preferable to have all buffer available as bicarbonate. In case of peritoneal dialysis, the presence of organic acids and dextrose in the same container will enhance the formation of glucose degradation products, which in turn may damage the peritoneal membrane.

Bicarbonate-based solutions are known which require the use of a stabilizing agent in addition to bicarbonate and other constituents, such as calcium and magnesium. For example, U.S. Pat. No. 4,959,175 discloses the use of stabilizing agents, such as glycylglycine, to prevent the precipitation of carbonates. European Patent Document No. EP 1166787 discloses the use of other types of stabilization agents, such as disodium hydrogen citrate. However, the use of stabilizing agents may have undesirable side effects.

Therefore, a need exists to provide improved bicarbonate-based solutions that can be readily manufactured, that can remain stable and sterile under storage conditions, and that can be readily and effectively used during medical therapy, such as dialysis therapy.

SUMMARY OF THE INVENTION

The present invention relates to improved bicarbonate-based solutions that can be used during medical therapy, particularly dialysis therapy, infusion therapy or other suitable medical therapies. The bicarbonate-based solutions of the present invention is provided as a single solution. The solution is provided in a container with a gas barrier. The single solution preferably includes a therapeutically effective amount of bicarbonate and calcium. It can also include a variety of other suitable constituents and combinations thereof, such as sodium, potassium, chloride, lactate, acetate and an osmotic agent.

The solution of the present invention is shelf stable. Applicants have discovered that the bicarbonate-based solutions of the present invention can remain stable for periods of up to about 3 months or greater. The bicarbonate-based solutions of the present invention can be formulated as a single solution that is both sterile and stable and further does not have to be mixed prior to use. This can facilitate ease of use during medical therapy, particularly during dialysis therapy.

The single solution can include a variety of different components in any suitable amount. Preferably, the single solution includes about 1 mmol/L to about 45 mmol/L of bicarbonate and about 0.1 mmol/L to about 2.5 mmol/L of calcium. In an embodiment, the single solution includes an additional constituent including, for example, 0 mmol/L to about 160 mmol/L of sodium, about 0 mmol/L to about 1.5 mmol/L of magnesium, about 0 mmol/L to about 5 mmol/L of potassium, about 0 mmol/L to about 130 mmol/L of chloride, about 0 mmol/L to about 45 mmol/L of lactate, about 0 mmol/L to about 45 mmol/L of acetate, about 0 mmol/L to about 100 g/L of an osmotic agent, like constituents and amounts and combinations thereof. In an embodiment, the pH of the single solution ranges from about 6.9 to about 7.9, preferably from about 7.0 to about 7.4.

An advantage of the present invention is to provide improved bicarbonate-based solutions.

Another advantage of the present invention is to provide a bicarbonate-based solution which can be packaged as a single ready to use solution.

Furthermore, an advantage of the present invention is to provide a bicarbonate-based single solution that is shelf stable for more than three months.

Still another advantage of the present invention is to provide a shelf stable bicarbonate-based single solution without requiring the use of a stabilizing agent.

Yet another advantage of the present invention is to provide a stable and sterile single bicarbonate-based solution that can be effectively used during dialysis therapy.

Yet still another advantage of the present invention is to provide improved methods for producing improved single and stable solutions at least containing bicarbonate and calcium.

A further advantage of the present invention is to provide medical therapies, such as dialysis therapy, that employ the use of a ready to use bicarbonate-based solution.

A still further advantage of the present invention is to provide methods of stabilizing dialysis solutions.

Additional features and advantages of the present invention are described in, and will be apparent from, the following Detailed Description of the Invention and the Figures.

DETAILED DESCRIPTION OF THE INVENTION

Figure 1:
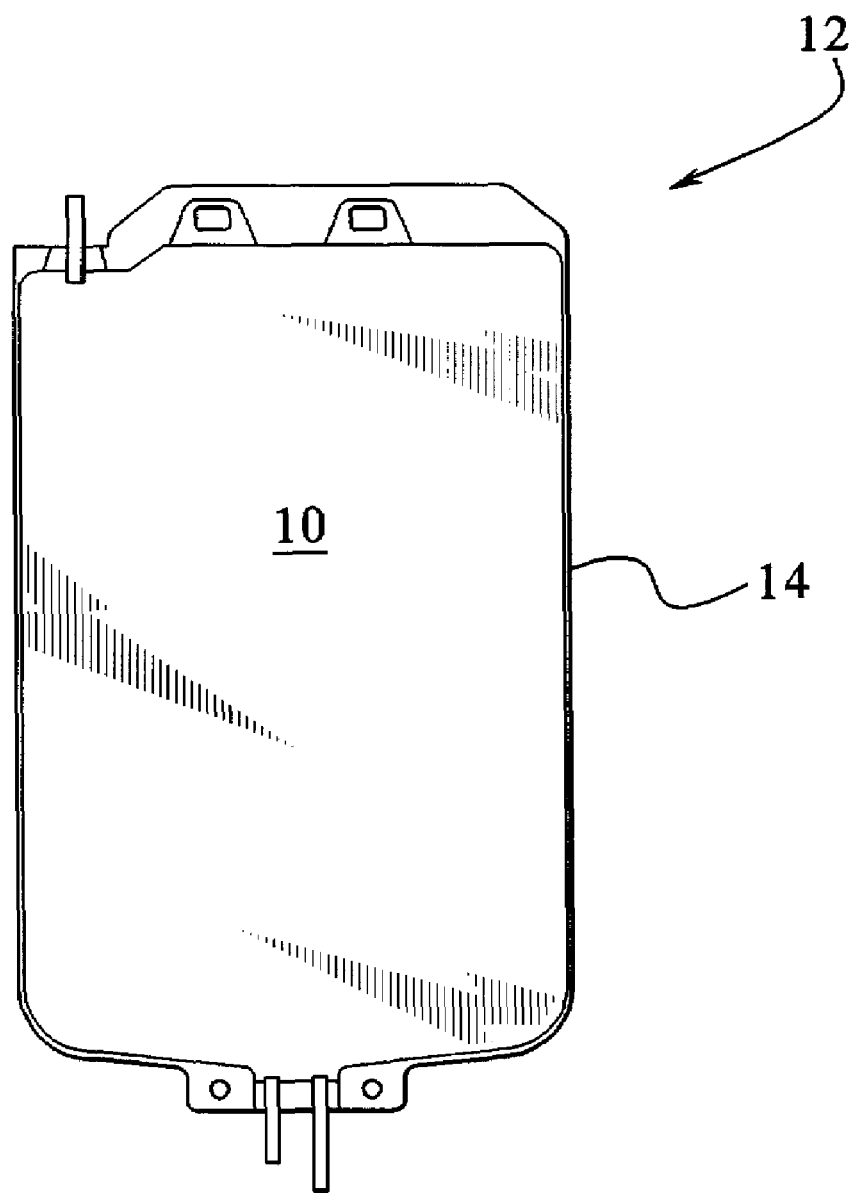
FIG. 1 illustrates a solution stored in a container with a gas barrier pursuant to an embodiment of the present invention.

The present invention provides improved bicarbonate-based solutions as well as methods of manufacturing and using same. In particular, the present invention relates to bicarbonate-based solutions that can be used as a part of medical therapy including dialysis therapy, infusion therapy or the like and are provided as ready to use solutions. In this regard, the solutions of the present invention are provided as a single, ready to use solution that does not require admixing. This can facilitate the ease in which the solution can be used during dialysis therapy.

The bicarbonate-based solutions of the present invention at least include a therapeutically effective amount of bicarbonate and calcium. The solution is stored as a single solution in a container with a gas barrier. As discussed in detail below, Applicants have discovered that the single bicarbonate-based solution of the present invention can remain shelf stable for extended periods of time, such as for periods of up to about three months or greater. Further, Applicants have demonstrated that the single bicarbonate-based solutions of the present invention can remain shelf stable without the use of a stabilizing agent, such as glycylglycine, citrate, disodium hydrogen citrate, combinations thereof or the like.

With respect to dialysis therapy, the present invention can be used in a variety of different dialysis therapies to treat kidney failure. Dialysis therapy as the term or like terms are used throughout the text is meant to include and encompass any and all forms of therapies to remove waste, toxins and excess water from the patient. The hemo therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. The bicarbonate-based solutions can also be used during peritoneal dialysis including, for example, continuous ambulatory peritoneal dialysis, automated peritoneal dialysis, continuous flow peritoneal dialysis and the like. Further, although the present invention, in an embodiment, can be utilized in methods providing a dialysis therapy for patients having chronic kidney failure or disease, it should be appreciated that the present invention can be used for acute dialysis needs, for example, in an emergency room setting.

As used herein, the term "infusion therapy" or other like terms means any medical therapy where a solution(s) is introduced or infused into a vein of a patient.

In an embodiment, the bicarbonate-based solution can be used as a dialysate during any suitable dialysis therapy. Alternatively, the solutions of the present invention can be administered or infused into a patient as a substitution fluid or the like during dialysis therapy, such as during hemofiltration, hemodiafiltration or other suitable dialysis therapy. In this regard, substitution fluids, infusion solutions or the like must necessarily be continuously fed to a patient as a substitute for an excessive amount of plasma water that is typically removed during continuous renal replacement therapy including continuous forms of hemofiltration or the like. In this regard, a proper water balance in the patient's body can be effectively maintained.

The stable and single solutions of the present invention can include a variety of different components in any suitable amount. In an embodiment, the single solution at least includes about 1 mmol/L to about 45 mmol/L of bicarbonate, preferably about 5 mmol/L to about 45 mmol/L of bicarbonate; and about 0.1 mmol/L to about 2.5 mmol/L of calcium, preferably about 0.2 mmol/L to about 2.0 mmol/L of calcium.

The single solution can include a variety of other constituents in addition to bicarbonate and calcium. For example, the single solution of the present invention can include about 0 mmol/L to about 160 mmol/L of sodium, preferably about 100 mmol/L to about 150 mmol/L of sodium; about 0 mmol/L to about 1.5 mmol/L of magnesium, preferably about 0.2 mmol/L to about 1.0 mmol/L of magnesium; about 0 mmol/L to about 5 mmol/L of potassium; about 0 mmol/L to about 130 mmol/L of chloride, preferably about 70 mmol/L to about 120 mmol/L of chloride; about 0 mmol/L to bout 45 mmol/L of lactate, preferably about 0 mmol/L to about 40 mmol/L of lactate; about 0 mmol/L to about 45 mmol/L of acetate; about 0 mmol/L to about 100 g/L of an osmotic agent and combinations thereof.

The osmotic agent can include any suitable material. In an embodiment, the osmotic agent can include glucose and polymers thereof, amino acids, peptides, glycerol, like compositions and combinations thereof. In an embodiment, the bicarbonate-based solution of the present invention has a pH that ranges from about 6.9 to about 7.9, preferably about 7.0 to about 7.4.

As previously discussed, the present invention provides a single and stable bicarbonate-based solution that can be readily and effectively used during dialysis therapy. In an embodiment, the single solution 10 is stored or packaged in a container 12 that has a gas barrier (not shown) in the container material 14 as illustrated in FIG. 1. The container can include any suitable container, such as a medical grade solution bag typically used to store and administer medical solutions, such as dialysis solutions. The container can be made of any suitable medical grade material, such as polyethylene and/or other suitable materials.

The container can be made with the gas barrier in any suitable way. Preferably, the gas barrier is in the container material as discussed above. Alternatively, the gas barrier can be an over pouch, a secondary liner or the like. The gas barrier can be composed of any suitable materials. In an embodiment, the gas barrier is composed of ethylvinyl acetate, polyvinyl dichloride, a copolymer of ethylvinyl acetate and polyvinyl dichloride, other suitable materials including polymeric materials and combinations thereof.

The stable and single bicarbonate-based solution of the present invention can be made in any suitable way. The bicarbonate-based solution is first prepared in any suitable manner by combining the requisite components, such as bicarbonate, calcium in addition to other additional constituents as previously discussed, to form the single solution. The components can be provided in concentrate form. The concentrates can then be mixed to form the single solution. For example, a concentrate including bicarbonate can be mixed with a concentrate including calcium. The single solution can then be packaged and/or stored in the container in a sterile manner. Further, the single solution can be sterilized in any suitable way, such as, filtration sterilization, heat sterilization, steam sterilization, radiation sterilization and/or like sterilization techniques.

As previously discussed, the single bicarbonate-based solutions of the present invention can remain stable for more than three months, preferably up to about 12 months or more. In this regard, the single bicarbonate-based solutions of the present invention remain ready-to-use even after an extended period of storage time allowing the single solution to be readily and effectively used during dialysis therapy.

By way of example and not limitation examples of Applicants' invention will now be set forth.

Stability Tests

Applicants have conducted a number of experiments to demonstrate the stable nature of the single solutions that are stored in a container with a gas barrier made in accordance with an embodiment of the present invention. As indicated below, Experimental Test I demonstrates the stable nature of the single solution of the present invention, and Experimental Test II provides a comparative test which demonstrates that the bicarbonate-based single solution of the present invention can remain shelf stable without requiring the use of a stabilizer agent.

Experimental Test I

A solution was made in accordance with an embodiment of the present invention. The solution contained the following constituents:

about 194 mmol/L of glucose, about 132 mmol/L of sodium, about 97 mmol/L of chloride, about 1.25 mmol/L of calcium, about 0.25 mmol/L of magnesium and about 38 mmol/L of bicarbonate The pH of the solution was adjusted with carbon dioxide and was filtered over a 0.22 micrometer filter in a sterile solution bag composed of ethylvinyl acetate, polyvinyl dichloride and polyethylene. The pH of the solution and the total calcium levels were periodically monitored over a 12 month period as indicated below in Table I.

TABLE I

| Parameter | Time in months | | | | | |
|---|---|---|---|---|---|---|
| | 0 | 1 | 3 | 7 | 10 | 12 |
| pH (25° C.) | 7.31 | 7.37 | 7.26 | 7.33 | 7.29 | 7.25 |
| Total calcium (mM) | 1.24 | 1.24 | 1.22 | 1.22 | 1.22 | 1.22 |

As shown in Table 1, the single solution remained stable over the 12 month period. In this regard, the pH and the total calcium levels remained relatively constant over this period.

Experimental Test II

Stability tests were conducted on three different bicarbonate-based solutions, namely, Test Solution IIA, Test Solution IIB and Test Solution IIC. Test Solution IIA included a bicarbonate-based solution with a stabilizing agent, namely glycylglycine. This test solution was made in accordance with the bicarbonate-based solutions disclosed in U.S. Pat. No. 4,959,175 ("Yatzidis"). Test Solutions IIB and IIC included bicarbonate-based solutions without a stabilizing agent, such as glycylglycine. These test solutions were made in accordance with an embodiment of the present invention.

Each of the test solutions was stored in a 2 liter solution bag that included a gas barrier in the bag material. The solution bag material was composed of ethylvinyl acetate, polyvinyl dichloride and polyethylene. The ethylvinyl acetate and polyvinyl dichloride components provided the gas barrier. The composition of the test solutions is indicated below:

| Constituents | mmol/L |
|---|---|
| Test Solutions IIA (Yatzidis) | |
| Glucose | 212.04 |
| Glycylglycerine | 10.00 |
| Sodium | 135.00 |
| Chloride | 110.5 |
| Potassium | 1.00 |
| Calcium | 1.75 |
| Magnesium | 0.50 |
| Bicarbonate | 30.00 |
| Test Solutions IIB (Embodiment of Present Invention) | |
| Glucose | 194.77 |
| Sodium | 132.00 |
| Chloride | 97.00 |
| Calcium | 1.25 |
| Magnesium | 0.25 |
| Bicarbonate | 38.00 |
| Test Solution IIC (Embodiment of Present Invention) | |
| Glucose | 194.77 |
| Sodium | 132.00 |
| Chloride | 97.00 |
| Calcium | 1.25 |
| Magnesium | 0.25 |
| Bicarbonate | 38.00 |

In general, the test solutions were prepared by dissolving the constituents in distilled water. Test Solution IIA had a pH of 7.27 before filling the bag and a pH of 7.45 after filling. With respect to Test Solution IIB, all constituents were added and the pH was then adjusted by bubbling carbon dioxide in solution to a pH of 7.28 before filling. The pH of Test Solution IIB after filling was 6.91. With respect to Test Solution IIC, all constituents were added except the bicarbonate which was slowly added thereafter under continuous bubbling of carbon dioxide in the solution to obtain a pH of 7.21 before filling. After filling, the pH was 7.02.

Each solution bag was filled with two liters of a test solution. Overall, nine solution bags were filled for each test solution. Test Solution IIA was filled under nitrogen pressure. Test Solutions IIB and IIC were filled under carbon dioxide pressure. Each test solution was sterilized by filtration on 0.22 micron filters. The solution bags filled with the test solutions were then squeezed and the pH was again checked at the end of filling each bag as discussed above. The solution bags filled with test solutions were stored without overpouches in cardboard boxes at 25° C. under 60% humidity.

The test solutions were monitored periodically for a number of parameters, such as pH, to evaluate the stability of the solutions over time. The parameters were monitored at time=0 (P0), 1 month (P1), 3 months (P3), 7 months (P7), 10 months (P10) and 12 months (P12) as indicated in Tables IIA-IIC below.

TABLE IIA

Test Solution IIA

| Tests | Units | P0 (deg) | P1 | P3 | P7 | P10 | P12 bag 1 | P12 bag 2 | P12 bag 3 | P12 bag 4 | P12 MEAN |
|---|---|---|---|---|---|---|---|---|---|---|---|
| Headspace volume | Ml | 24 | — | — | — | — | — | — | — | — | — |
| Partial CO2 pressure of the colution at | MmHg | 53.5 | 51.9 | 48.8 | 49.2 | 83.4 | 40.2 | 42.7 | 41.3 | 40.9 | 41.3 |
| pH of the solution at 25° | — | 7.177 | 7.175 | 7.214 | 7.182 | 6.853 | 7.229 | 7.218 | 7.235 | 7.202 | 7.221 |
| Particles >2 μm | Part/ml | 48 | 24 | 36 | 12 | 371 | 13 | 19 | 31 | 28 | 23 |
| Particles >5 μm | Part/ml | 16 | 8 | 11 | 3 | 100 | 3 | 4 | 8 | 7 | 6 |
| Particles >10 μm | Part/ml | 1 | 1 | 0 | 0 | 13 | 1 | 0 | 1 | 1 | 1 |
| Particles >20 μm | Part/ml | 0 | 0 | 0 | 0 | 2 | 0 | 0 | 0 | 0 | 0 |
| Particles >25 μm | Part/ml | 0 | 0 | 0 | 0 | 0 | 0 | 0 | 0 | 0 | 0 |
| Visual inspection black and white | — | Pass | Pass | Pass | Pass | Pass | Pass | Pass | Pass | Pass | — |
| Visual inspection polarized light | — | Pass | Pass | Pass | Pass | Pass | Pass | Pass | Pass | Pass | — |
| Total NaHCO3 | mM | 27.75 | 27.97 | 29.34 | 27.54 | 21.57 | 26.22 | 27.60 | 28.57 | 27.60 | 27.50 |
| Color | Klett | 2 | 2 | 6 | 7 | 8 | 5 | 5 | 4 | 4 | 5 |
| Total calcium | G/l | 0.254 | 0.252 | 0.250 | 0.262 | 0.254 | 0.258 | 0.264 | 0.262 | 0.265 | 0.262 |

TABLE IIA-continued

Test Solution IIA

| Tests | Units | PO (deg) | P1 | P3 | P7 | P10 | P12 bag 1 | P12 bag 2 | P12 bag 3 | P12 bag 4 | MEAN |
|---|---|---|---|---|---|---|---|---|---|---|---|
| Total magnesium | G/l | 0.1000 | 0.1063 | 0.1063 | 0.1017 | 0.0997 | 0.0961 | 0.1029 | 0.1014 | 0.1025 | 0.1007 |
| Ionized calcium | MM | 1.61 | 1.57 | 1.60 | 1.59 | 1.63 | 1.57 | 1.57 | 1.57 | 1.59 | 1.58 |

TABLE IIB

Test Solution IIB

| Tests | Units | PO (bag) | P1 | P3 | P7 | P10 | P12 bag 1 | P12 bag 2 | P12 bag 3 | MEAN |
|---|---|---|---|---|---|---|---|---|---|---|
| Headspace volume | Ml | 20 | — | — | — | — | — | — | — | — |
| Partial CO2 pressure of the solution at 25° C. | mmHg | 57.5 | 49.4 | 61.3 | 49.9 | 47.2 | 65.5 | 50.5 | 57.4 | 57.8 |
| pH of the solution at 25° | — | 7.313 | 7.366 | 7.259 | 7.325 | 7.291 | 7.187 | 7.301 | 7.253 | 7.247 |
| Particles> 2 µm | part/ml | 24 | 16 | 30 | 9 | 62 | 23 | 30 | 334 | 129 |
| Particles> 5 µm | part/ml | 8 | 5 | 9 | 4 | 10 | 3 | 11 | 44 | 19 |
| Particles> 10 µm | part/ml | 3 | 0 | 0 | 1 | 0 | 0 | 4 | 4 | 3 |
| Particles> 20 µm | part/ml | 0 | 0 | 0 | 0 | 0 | 0 | 0 | 0 | 0 |
| Particles> 25 µm | part/ml | 0 | 0 | 0 | 0 | 0 | 0 | 0 | 0 | 0 |
| Visual inspection black and white | — | Pass | Pass | Pass | Pass | Pass | Pass | Pass | Pass | — |
| Visual inspection polarized light | — | Pass | Pass | Pass | Pass | Pass | Pass | Pass | Pass | — |
| Total NaHCO3 | mM | 37.67 | 39.58 | 37.29 | 36.83 | 36.75 | 36.36 | 36.94 | 37.22 | 36.84 |
| Color | Klett | 4 | 4 | 6 | 8 | 3 | 4 | 3 | 5 | 4 |
| Total calcium | g/l | 0.183 | 0.183 | 0.179 | 0.179 | 0.179 | 0.181 | 0.180 | 0.179 | 0.180 |
| Total magnesium | g/l | 0.0509 | 0.0532 | 0.0536 | 0.0527 | 0.0511 | 0.0516 | 0.0491 | 0.0490 | 0.0499 |
| Ionized calcium | mM | 1.12 | 1.07 | 1.10 | 1.10 | 1.05 | 1.08 | 1.05 | 1.08 | 1.07 |

TABLE IIC

Test Solution IIC

| Tests | Units | PO (bag) | P1 | P3 | P7 | P10 | P12 bag 1 | P12 bag 2 | P12 Bag 3 | MEAN |
|---|---|---|---|---|---|---|---|---|---|---|
| Headspace volume | M1 | 25 | — | — | — | — | — | — | — | — |
| Partial CO2 pressure of the solution at 25° C. | MmHg | 46.9 | 62.3 | 69.8 | 89.6 | 48.7 | 52.5 | 63.8 | 59.6 | 58.6 |
| pH of the solution at 25° | — | 7.433 | 7.298 | 7.225 | 7.107 | 7.343 | 7.310 | 7.237 | 7.261 | 7.269 |
| Particles> 2 µm | part/ml | 210 | 18 | 16 | 28 | 42 | 28 | 14 | 22 | 21 |
| Particles> 5 µm | part/ml | 17 | 6 | 3 | 8 | 9 | 5 | 2 | 3 | 3 |
| Particles> 10 µm | part/ml | 1 | 0 | 0 | 0 | 1 | 0 | 0 | 1 | 0 |
| Particles> 20 µm | part/ml | 0 | 0 | 0 | 0 | 0 | 0 | 0 | 0 | 0 |
| Particles> 25 µm | part/ml | 0 | 0 | 0 | 0 | 0 | 0 | 0 | 0 | 0 |
| Visual inspection black and white | — | Pass | Pass | Pass | Pass | Pass | Pass | Pass | Pass | — |
| Visual inspection polarized light | — | Pass | Pass | Pass | Pass | Pass | Pass | Pass | Pass | — |
| Total NaHCO3 | mM | 39.48 | 39.43 | 39.23 | 39.05 | 39.35 | 38.77 | 39.01 | 39.3 | 39.03 |
| Color | Klett | 7 | 4 | 6 | 7 | 3 | 4 | 3 | 4 | 4 |
| Total calcium | g/l | 0.180 | 0.182 | 0.179 | 0.187 | 0.179 | 0.178 | 0.179 | 0.181 | 0.179 |
| Total magnesium | g/l | 0.500 | 0.0529 | 0.0536 | 0.0520 | 0.0512 | 0.0485 | 0.0489 | 0.0519 | 0.0498 |
| Ionized calcium | mM | 1.10 | 1.08 | 1.09 | 1.11 | 1.07 | 1.05 | 1.07 | 1.08 | 1.07 |

Overall, the test results indicate that the bicarbonate-based test solutions with and without a stabilizing agent remained relatively stable for at least 12 months at 25° C. This demonstrates that the use of a stabilizing agent, such as glycylglycine, to stabilize bicarbonate-based solutions is not required.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A container including a bicarbonate-based solution comprising:
   a single solution comprising about 0 g/L to about 100 g/L of an osmotic agent, about 1 mmol/L to about 45 mmol/L of bicarbonate, about 0.1 mmol/L to about 2.5 mmol/L of calcium, 100 mmol/L to about 150 mmol/L of sodium, about 0.2 mmol/L to about 1.0 mmol/L of magnesium, about 70 mmol/L to about 120 mmol/L of chloride, about 0 mmol/L to about 5 mmol/L of potassium, and stored in a single chamber of the container having a gas barrier that is not in a form of an over pouch, wherein the single solution is heat sterilized in the single chamber and remains stable at a pH ranging from about 6.9 to about 7.9 for at least three months after heat sterilization, wherein the pH is adjusted prior to heat sterilization, and wherein the single solution excludes organic acids except for amino acids.

2. The container of claim 1 wherein the amount of calcium is about 0.2 mmol/L to about 2 mmol/L.

3. The container of claim 1 wherein the bicarbonate-based solution comprises a dialysis solution.

4. The container of claim 1 wherein the bicarbonate-based solution comprises an infusion solution.

5. The container of claim 1 wherein the osmotic agent is selected from the group consisting of glycerol, an amino acid, glucose, and combinations thereof.

6. A method of providing a bicarbonate-based solution, the method comprising:
   forming a single solution comprising about 0 g/L to about 100 g/L of an osmotic agent, about 1 mmol/L to about 45 mmol/L of bicarbonate, about 0.1 mmol/L to about 2.5 mmol/L of calcium, about 100 mmol/L to about 150 mmol/L of sodium, about 0.2 mmol/L to about 1.0 mmol/L of magnesium, about 70 mmol/L to about 120 mmol/L of chloride, about 0 mmol/L to about 5 mmol/L of potassium, wherein the single solution excludes organic acids except for amino acids; and
   storing the single solution in a container having a gas barrier that is not in a form of an over pouch wherein the single solution is heat sterilized in a single chamber of the container, wherein the single solution remains stable for at least three months after heat sterilization at a pH ranging from about 6.9 to about 7.9, and wherein the pH is adjusted prior to heat sterilization.

7. The method of claim 6 wherein the single solution can be used during dialysis therapy.

8. The method of claim 6 wherein the single solution can be used during infusion therapy.

9. The method of claim 6 wherein the osmotic agent is selected from the group consisting of glycerol, an amino acid, glucose, and combinations thereof.

10. A method of storing a dialysis solution, the method comprising:
    preparing a single solution comprising about 0 g/L to about 100 g/L of an osmotic agent, about 1 mmol/L to about 45 mmol/L of bicarbonate, about 0.1 mmol/L to about 2.5 mmol/L of calcium, about 100 mmol/L to about 150 mmol/L of sodium, about 0.2 mmol/L to about 1.0 mmol/L of magnesium, about 70 mmol/L to about 120 mmol/L of chloride, and about 0 mmol/L to about 5 mmol/L of potassium, wherein the single solution excludes organic acids except for amino acids;
    packaging the single solution in a container having a gas barrier that is not in a form of an over pouch, wherein the single solution is heat sterilized in a single chamber of the container; and
    storing the single solution in the container wherein the single solution remains stable at a pH that ranges from about 6.9 to about 7.9 in the container for at least 3 months prior to use, and wherein the pH is adjusted prior to heat sterilization.

11. The method of claim 10 wherein the single solution includes a dialysis solution.

12. The method of claim 10 wherein the single solution includes an infusion solution.

13. The method of claim 10 wherein the osmotic agent is selected from the group consisting of glycerol, an amino acid, glucose, and combinations thereof.

14. A method of providing dialysis therapy to a patient, the method comprising:
    providing a dialysis solution that does not require admixing, the dialysis solution comprising about 0 g/L to about 100 g/L of an osmotic agent, about 1 mmol/L to about 45 mmol/L of bicarbonate, about 0.1 mmol/L to about 2.5 mmol/L of calcium, about 0 mmol/L to about 5 mmol/L of potassium, about 100 mmol/L to about 150 mmol/L of sodium, about 0.2 mmol/L to about 1.0 mmol/L of magnesium, and about 70 mmol/L to about 120 mmol/L of chloride, wherein the dialysis solution is stored in a container having a gas barrier that is not in a form of an over pouch, wherein the dialysis solution is heat sterilized in a single chamber of the container and remains stable for at least three months at a pH ranging from about 6.9 to about 7.9, wherein the pH is adjusted prior to heat sterilization, and wherein the dialysis solution excludes organic acids except for amino acids; and
    providing a therapeutically effective amount of the dialysis solution to a patient in need of same.

15. The method of claim 14 wherein the dialysis solution is used during dialysis therapy selected from the group consisting of hemodialysis, hemofiltration, hemodiafiltration, peritoneal dialysis and continuous renal replacement therapy.

16. The method of claim 14 wherein the dialysis solution is used as a dialysate.

17. The method of claim 14 wherein the dialysis solution is infused into the patient as an infusion solution.

18. The method of claim 14 wherein the osmotic agent is selected from the group consisting of glycerol, an amino acid, glucose, and combinations thereof.

* * * * *